(12) United States Patent
Lamprich et al.

(10) Patent No.: US 7,918,890 B2
(45) Date of Patent: *Apr. 5, 2011

(54) SPINAL DISC PROSTHESIS AND METHODS

(75) Inventors: Lonnie Jay Lamprich, Oklahoma City, OK (US); Bradley Keith Lamprich, Oklahoma City, OK (US)

(73) Assignee: Lamprich Medical, LLC, Oklahoma City, OK (US)

( * ) Notice: Subject to any disclaimer, the term of this patent is extended or adjusted under 35 U.S.C. 154(b) by 1052 days.

This patent is subject to a terminal disclaimer.

(21) Appl. No.: 10/995,886

(22) Filed: Nov. 23, 2004

(65) Prior Publication Data

US 2006/0025864 A1    Feb. 2, 2006

Related U.S. Application Data

(63) Continuation-in-part of application No. 10/899,898, filed on Jul. 27, 2004, now Pat. No. 7,172,628.

(51) Int. Cl.
*A61F 2/44* (2006.01)
(52) U.S. Cl. ..................... 623/17.16
(58) Field of Classification Search .... 623/17.11–17.16, 623/14.12, 16.11, 23.72, 23.75, 23.76, 23.6, 623/23.61, 23.62; 606/99, 86 R–96, 63, 606/62, 246–249
See application file for complete search history.

(56) References Cited

U.S. PATENT DOCUMENTS

| | | | |
|---|---|---|---|
| 4,772,287 A | 9/1988 | Ray et al. | |
| 5,015,255 A | 5/1991 | Kuslich | |
| 5,059,193 A | 10/1991 | Kuslich | |
| 5,489,307 A | 2/1996 | Kuslich et al. | |
| 5,549,679 A | 8/1996 | Kuslich | |
| 5,558,674 A | 9/1996 | Heggeness et al. | |
| 5,645,597 A | 7/1997 | Krapiva | |
| 5,674,295 A | 10/1997 | Ray et al. | |
| 5,772,661 A | 6/1998 | Michelson | |
| 5,865,846 A | 2/1999 | Bryan et al. | |
| 5,879,353 A | 3/1999 | Terry | |
| 5,928,284 A | 7/1999 | Mehdizadeh | |
| 5,991,997 A | 11/1999 | Schley et al. | |

(Continued)

FOREIGN PATENT DOCUMENTS

EP     0307241     3/1989

(Continued)

OTHER PUBLICATIONS

M. Neo et al., The Use of an Aiming Device in Posterior Atlantoaxial Transarticular Screw Fixation, 97 J. Neurosurg. 123 (Jul. 2002).

(Continued)

*Primary Examiner* — Alvin J Stewart
(74) *Attorney, Agent, or Firm* — McAfee & Taft

(57) ABSTRACT

The present invention provides novel spinal disc prosthesis comprising two solid compressible cylinders and methods. A method of the invention for placing the solid compressible cylinders between adjacent spinal vertebrae comprises the steps of forming an enlarged partially circular space from the back and to one side of the space between adjacent spinal vertebrae previously occupied by a degenerated disc, forming additional spaces within the interiors of the adjacent vertebrae, placing a solid compressible cylinder in the spaces within the interiors of the adjacent vertebrae and repeating the above procedure on the other side of the space between the vertebrae.

16 Claims, 6 Drawing Sheets

U.S. PATENT DOCUMENTS

| | | | |
|---|---|---|---|
| 6,004,326 | A | 12/1999 | Castro et al. |
| 6,110,178 | A | 8/2000 | Zech et al. |
| 6,231,609 | B1 | 5/2001 | Mehdizadeh |
| 6,261,311 | B1 | 7/2001 | Sharkey et al. |
| 6,315,795 | B1 | 11/2001 | Scarborough et al. |
| 6,368,350 | B1 | 4/2002 | Erickson et al. |
| 6,402,785 | B1 | 6/2002 | Zdeblick et al. |
| 6,468,276 | B1 | 10/2002 | McKay |
| 6,478,822 | B1 | 11/2002 | Leroux |
| 6,482,234 | B1 | 11/2002 | Weber et al. |
| 6,537,279 | B1 | 3/2003 | Michelson |
| 6,613,089 | B1 * | 9/2003 | Estes et al. ............... 623/17.11 |
| 6,695,851 | B2 | 2/2004 | Zdeblick et al. |
| 6,746,451 | B2 | 6/2004 | Middleton et al. |
| 6,758,863 | B2 | 7/2004 | Estes et al. |
| 6,764,514 | B1 * | 7/2004 | Li et al. ............... 623/17.12 |
| 2002/0045942 | A1 | 4/2002 | Ham |
| 2003/0195520 | A1 | 10/2003 | Boyd et al. |
| 2004/0148028 | A1 | 7/2004 | Ferree et al. |
| 2004/0153064 | A1 | 8/2004 | Foley et al. |
| 2004/0215344 | A1 | 10/2004 | Hochschuler et al. |
| 2005/0055099 | A1 | 3/2005 | Ku |
| 2005/0059972 | A1 | 3/2005 | Biscup |
| 2006/0030862 | A1 | 2/2006 | De Villiers et al. |

FOREIGN PATENT DOCUMENTS

| | | |
|---|---|---|
| EP | 1 092 395 B1 | 4/2004 |
| WO | WO 2007/089858 A3 | 7/2008 |

OTHER PUBLICATIONS

Y. Ishida et al., Critical Analysis of Extensive Cervical Laminectomy, 24 Neurosurgery 215 (Feb. 1989).

B.L. Allen et al., The Biomechanics of Decompressive Laminectomy, 12 Spine 803 (Oct. 1987).

* cited by examiner

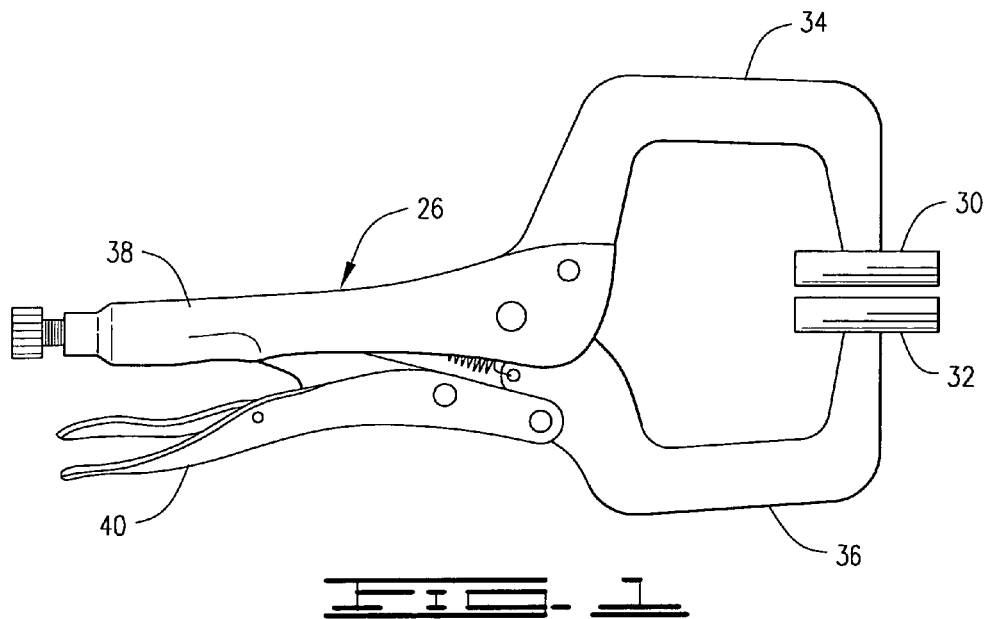
FIG-1
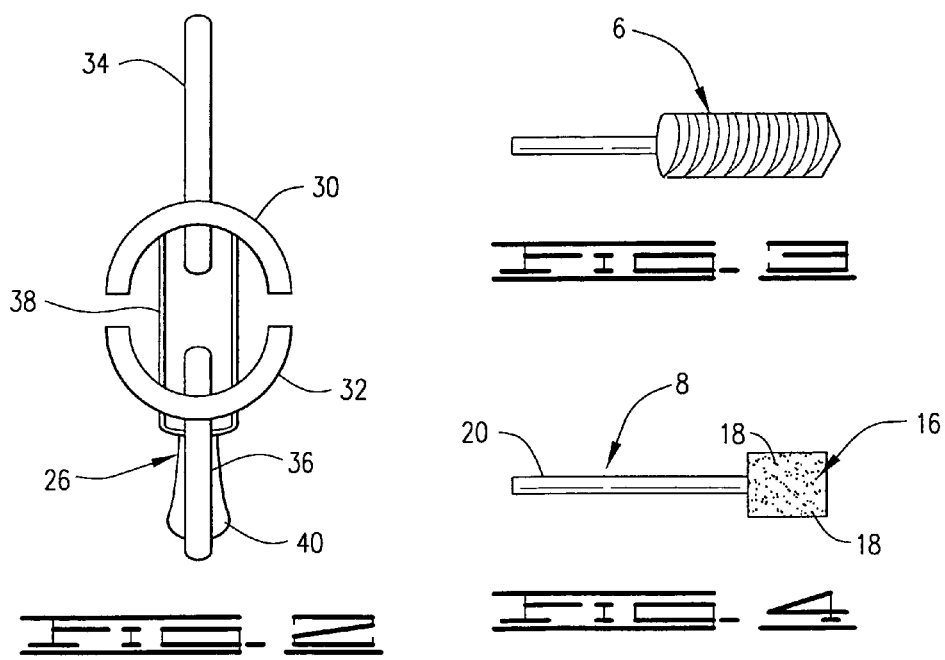
FIG-2
FIG-3
FIG-4

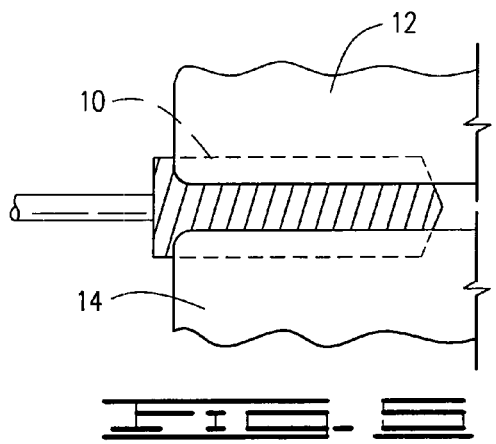
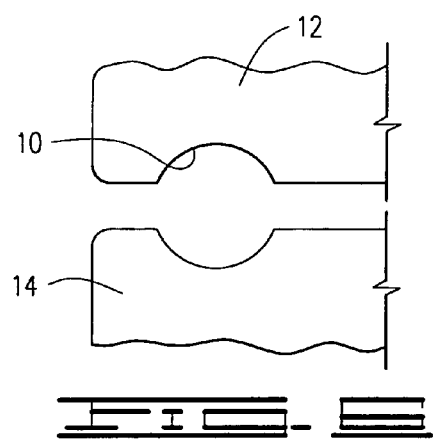
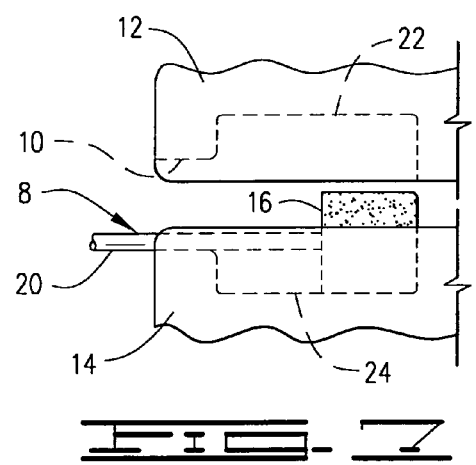
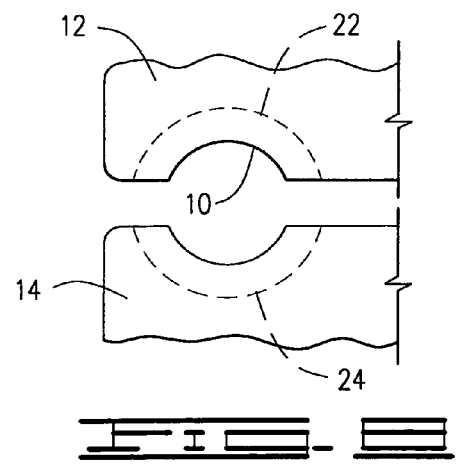
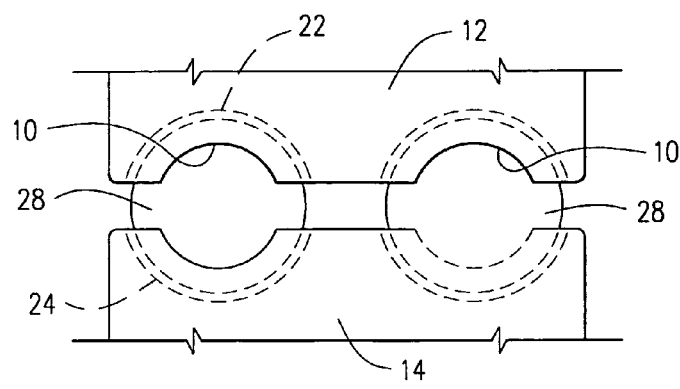

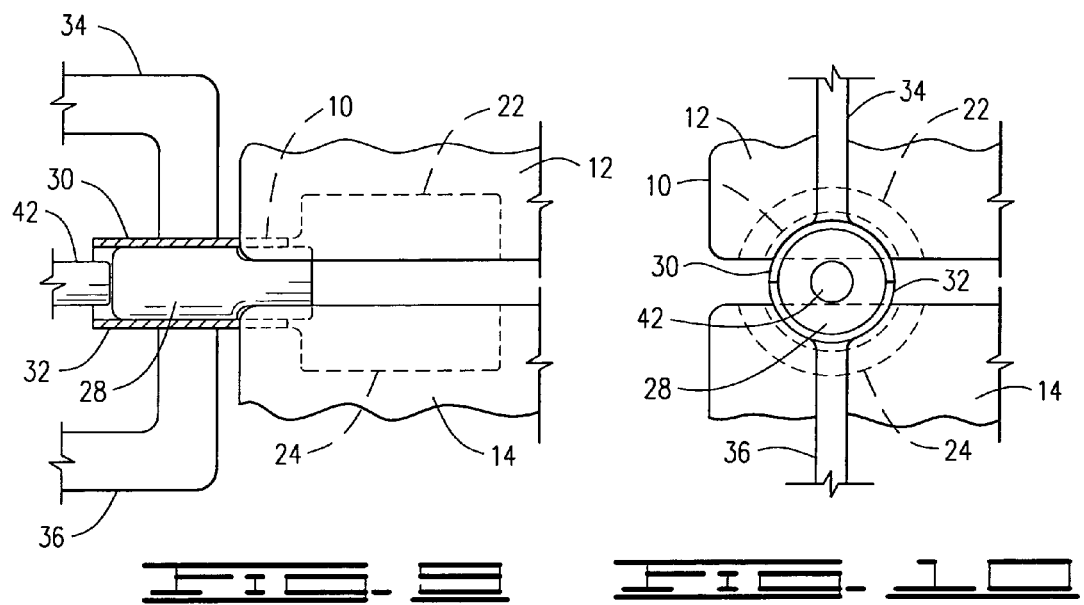
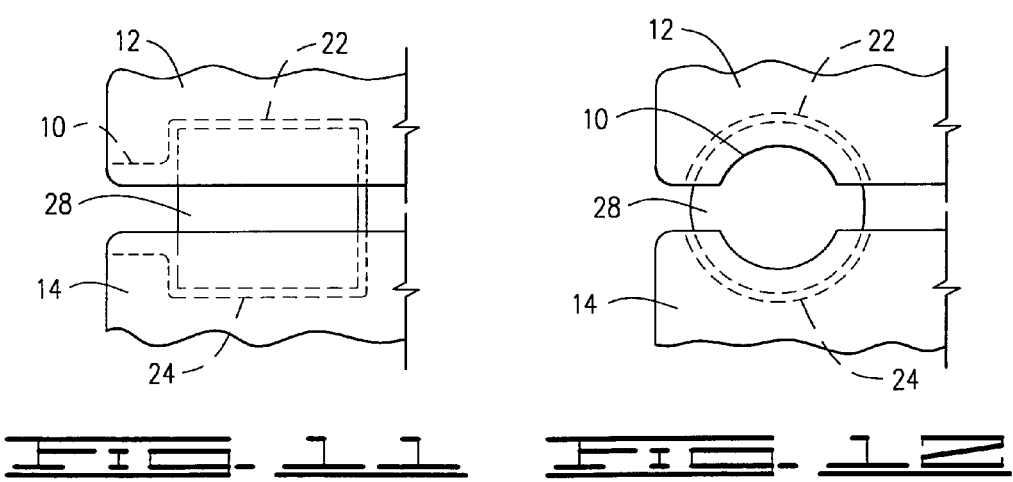

SPINAL DISC PROSTHESIS AND METHODS

This Application is a Continuation-In-Part of application Ser. No. 10/899,898 filed on Jul. 27, 2004 now U.S. Pat. No. 7,172,628.

BACKGROUND OF THE INVENTION

1. Field of the Invention

The present invention relates to a novel spinal disc prosthesis and to a novel method of placing the prosthesis between adjacent vertebrae.

2. Description of the Prior Art

The vertebrae of the spine are each separated by a relatively soft disc which acts as a joint that allows the spine to flex, extend, bend laterally and rotate. Each disc includes a tough outer fibrous ring that binds the adjacent vertebrae together. The fibrous portion consists of overlapping multiple plys and are attached to the vertebrae in a manner that resists torsion whereby half of the angulated fibers making up the ring will tighten when the vertebrae rotate in either direction relative to each other. The inside of the disc has a high water content which aids in the load-bearing and cushioning properties of the disc. However, one or more discs in the spine can be displaced or damaged due to trauma or disease. A disc herniation occurs when the fibers are weakened or torn and the disc becomes permanently stressed, extended or extruded out of its normal confines. A herniated or slipped disc can compress a spinal nerve resulting in pain, loss of muscle control, or even paralysis. Also, the disc degeneration causes it to lose water and deflate. As a result, the height of the disc decreases causing it to buckle. As the buckling takes place, radial or annular tears may occur and contribute to persistent and disabling pain.

While a variety of procedures and disc prostheses have been developed and used heretofore, they often involve fixed rigid approaches and systems which do not restore normal function and require long and complex operations. Thus, there is a continuing need for improved disc prosthesis and a method of placing the prosthesis between vertebrae which is relatively simple and provides normal spine function without pain or disability.

SUMMARY OF THE INVENTION

The present invention provides improved spinal disc prosthesis and methods of placing the prosthesis between adjacent vertebrae which meet the needs described above and overcome the deficiencies of the prior art.

A method of the present invention for placing a disc prosthesis comprising two solid compressible cylinders between adjacent spinal vertebrae basically comprises the following steps. An enlarged partially circular space is formed from the back and to one side of the space between adjacent vertebrae previously occupied by a degenerated disc using a drill bit. Additional spaces within the interiors of the adjacent vertebrae that intersect the enlarged space between the vertebrae are then formed using a router bit having a small shaft. Next, one of the two solid compressible cylinders is placed in the spaces within the interiors of the adjacent vertebrae using a thumbscrew apparatus for compressing the cylinder. The compressed cylinder is pushed into the spaces between the interiors of the adjacent vertebrae by way of the enlarged space between the vertebrae wherein the compressed cylinder expands to its original shape. Thereafter, the procedure described above is repeated on the other side of the space between the adjacent vertebrae. The two compressible cylinders are trapped in the spaces within the interiors of the adjacent vertebrae and function in the same manner as a normal vertebrae disc.

Another method of the present invention for placing a disc prosthesis comprised of two solid compressible cylinders between adjacent spinal vertebrae is comprised of the following steps. An enlarged partially circular space is formed from the back and to one side of the space between adjacent vertebrae previously occupied by a degenerated disc using a drill bit. Additional spaces within the interiors of the adjacent vertebrae that intersect the enlarged space between the vertebrae are formed using a router bit having a small shaft. A thumbscrew apparatus is provided for compressing the disc prosthesis, i.e., one of the two solid compressible cylinders to a size slightly smaller than the enlarged substantially circular space between the adjacent spinal vertebrae. Next, one of the solid compressible cylinders is compressed using the thumbscrew apparatus and the compressed cylinder is pushed into the enlarged circular space between the adjacent spinal vertebrae and into the spaces within the interiors of the adjacent vertebrae wherein the compressed cylinder expands to its original shape. Thereafter, the procedure described above is repeated on the other side of the space between the adjacent vertebrae. The two compressible cylinders are trapped in the spaces within the interiors of the adjacent vertebrae and function in the same manner as a normal vertebrae disc.

The spinal disc prosthesis of this invention comprises two solid compressible cylinders of a size for insertion in adjacent spaces within the interiors of adjacent vertebrae.

The objects, features and advantages of the present invention will be readily apparent to those skilled in the art upon a reading of the description of preferred embodiments which follows.

BRIEF DESCRIPTION OF THE DRAWINGS

FIG. 1 is a side view of a pliers apparatus having opposing semi-cylindrical jaws for compressing a disc prosthesis comprising two solid compressible cylinders and for placing the solid compressible cylinders into spaces within the interiors of adjacent vertebrae.

FIG. 2 is a front view of the pliers apparatus of FIG. 1.

FIG. 3 is a drill bit for forming an enlarged partially circular space between adjacent spinal vertebrae.

FIG. 4 is a router having a very small diameter shaft for forming additional spaces within the interiors of the adjacent vertebrae.

FIG. 5 is a partial side view of adjacent vertebrae illustrating the enlarged partially circular space formed using the drill bit.

FIG. 6 is a partial back view of the adjacent vertebrae after the enlarged partially circular space between the adjacent spinal vertebrae has been formed.

FIG. 7 is a partial side view of adjacent vertebrae showing the additional spaces formed by the router within the interiors of the adjacent vertebrae that intersect the enlarged space between the vertebrae.

FIG. 8 is a partial back view of the adjacent vertebrae after the enlarged partially circular space between the adjacent spinal vertebrae and the additional spaces within the interiors of the adjacent vertebrae have been formed.

FIG. 9 is a partial side view of the adjacent vertebrae illustrating a compressed solid compressible cylinder being pushed with a rod through the clamped together opposing cylindrical jaws of the pliers apparatus and through the enlarged partially circular space between the adjacent spinal vertebrae into the additional spaces within interiors of the adjacent vertebrae.

FIG. 10 is a partial back view of the adjacent vertebrae showing the compressed solid compressible cylinder being pushed into the additional spaces within the interiors of the adjacent vertebrae.

FIG. 11 is a partial side view of the adjacent vertebrae after the solid compressible cylinder has been placed and expanded in the spaces within the interiors of the adjacent vertebrae.

FIG. 12 is a back view of the solid compressible cylinder and the adjacent vertebrae illustrated in FIG. 11.

FIG. 13 is a back view of the spine showing the compressible disc prosthesis of the present invention, i.e., two solid compressible cylinders, placed between adjacent vertebrae.

DESCRIPTION OF PREFERRED EMBODIMENTS

Figure 14A:
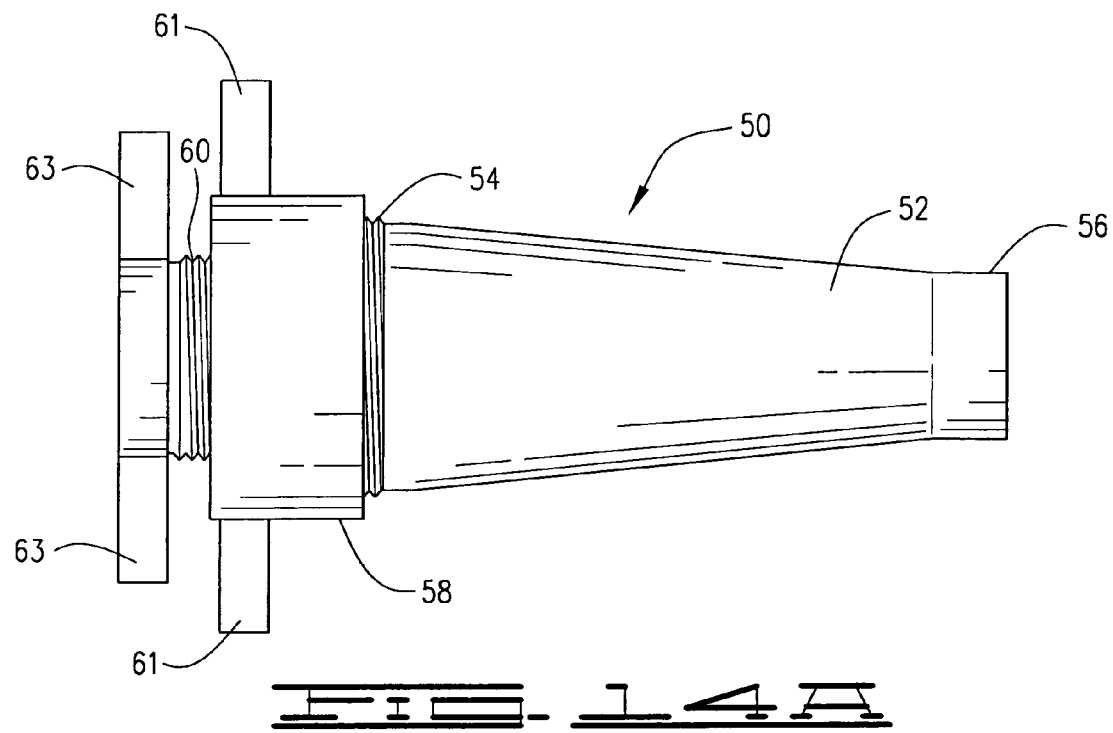
FIG. 14A is a side view of an alternate thumbscrew apparatus for compressing a disc prosthesis comprising two solid compressive cylinders and for placing the solid compressible cylinders into spaces within the interiors of adjacent vertebrae.

The present invention provides disc prosthesis and methods of placing the disc prosthesis between adjacent spinal vertebrae wherein the natural disc separating and cushioning the adjacent vertebrae has degenerated. The loss of the natural disc causes the adjacent vertebrae in the spine to lose physiologic motion and stability and pain to be experienced.

A variety of surgical procedures have heretofore been utilized to provide cushioning between adjacent vertebrae by placing a disc prosthesis between the vertebrae or to solve the problem by fusing or connecting the vertebrae together. Generally, the surgical procedures have been partially successful, but they have not restored the physiological function of normal cushioning and stabilization, i.e., allowing normal motion and maintaining load-cushioning in all directions of force.

By the present invention, an improved spinal disc prosthesis and method of placing the prosthesis are provided that allows normal cushioning and stabilization. The method of this invention for placing the prosthesis between adjacent spinal vertebrae greatly reduces costs as compared to rigid fixation and other surgical techniques heretofore utilized and provides a relatively simple and easily accomplished surgical procedure for providing normal motion and cushioning for a long period of time. Further, after a period of time, if degeneration of the disc prosthesis occurs, the disc prosthesis is easily and quickly replaced utilizing microendoscopic paramedian approach technologies. The procedure of this invention for placing a disc prosthesis between adjacent spinal vertebrae or replacing a previous disc prosthesis involves direct exposure of nerve roots or the like as desired and the entire procedure may be accomplished by means of a back approach only.

Prior to placing the disc prosthesis of this invention between adjacent spinal vertebrae, a number of known and heretofore used steps are performed. The first such step is the removal of the degenerated disc between adjacent vertebrae. The standard procedure used is a bilateral microscopic lumbar hemilaminotomy foramenotomy discectomy. This standard procedure is utilized to remove a portion of the disc. Once the portion of the disc has been removed, another well known instrument known as a disc distractor is utilized to move the vertebrae apart. The distractor is placed between the adjacent vertebrae on the side opposite to that on which the work is started. The distractor is inserted and turned 90° to push the vertebrae apart. Finally, the vertebrae are lined up using X-ray equipment and a steel cylinder and collar can be placed on the adjacent vertebrae. The collar includes triangular tangs that stick into the bone to hold the collar in place. When used, the collar serves as a drill guide and a protective device. Once the procedures described above have been completed, the method of the present invention is utilized to place a disc prosthesis of this invention between the adjacent vertebrae.

The first step of the method of this invention involves the formation of an enlarged partially cylindrical space between the adjacent spinal vertebrae separated by the space previously occupied by a degenerated disc. With the space held apart by the previously described distractor, an enlarged space from the back of the vertebrae is formed in the space between the adjacent vertebrae. That is, using a drill bit, preferably of a size of 9/16 inch in diameter, a partially circular opening in the space between the vertebrae is formed from the back to near the front of the adjacent vertebrae on one side thereof. The space extends into the adjacent vertebrae from back to front in a length of about 2/3 of the width of the vertebrae. Referring to the drawings, the drill bit designated by the numeral 6 is illustrated in FIG. 3 and the space 10 formed in the upper and lower spaced apart vertebrae 12 and 14 using the drill bit 6 is illustrated in FIGS. 5 and 6.

The next step involves the router 8 shown in FIG. 4. The enlarged portion 16 of the router 8 is cylindrical and the outside surfaces of the portion 16 include a plurality of cutting edges or sharp points 18. The enlarged cylindrical portion 16 is of a size equal to or slightly smaller than the partial circular space 10. A very small shaft 20 is attached to the enlarged cylindrical portion 16, i.e., a shaft of a size of about 1/8 of an inch in diameter.

Referring now to FIG. 7, the router 8 is illustrated within the interiors of additional spaces 22 and 24 formed within the adjacent vertebrae 12 and 14 by the router 8. That is, the enlarged cylindrical portion 16 of the router 8 is inserted in the enlarged space 10 formed between the vertebrae 12 and 14 by the drill bit 6. The router 8 is then moved up and down within the interiors of the adjacent vertebrae 12 and 14 whereby the spaces 22 and 24 are formed in the adjacent vertebrae which intersect the horizontal space 10. A back view of the adjacent vertebrae 12 and 14 after the space 10 and the spaces 22 and 24 have been formed is shown in FIG. 8. Because the shaft 20 of the router 8 has a very small diameter, the enlarged cylindrical portion 16 having cutting edges or points 18 thereon can extend into the adjacent vertebrae 12 and 14 the distances required to form the spaces 22 and 24.

Referring now to FIGS. 1 and 2, a pliers apparatus 26 for compressing the disc prosthesis, i.e., the solid compressible cylinders 28 which are formed of a rubbery substance, into smaller cylindrical shapes of a size that can be pushed through the opening 10 into the spaces 22 and 24 is illustrated. The pliers apparatus 26 is similar to conventional vise-grip pliers except that the jaws 30 and 32 are semi-cylindrical for compressing the solid compressible cylinders 28. The jaws 30 and 32 are positioned adjacent to each other by movable arms 34 and 36 connected thereto that open and close the jaws. The arms 34 and 36 are in turn connected to the handles 38 and 40 of the pliers 26. The inside surfaces of jaws 30 and 32 are preferably coated with "TEFLON™" to facilitate pushing a compressed disc prosthesis out of the closed jaws.

In the use of the pliers apparatus 26, a solid compressible cylinder 28 of this invention shown in its non-compressed form in FIGS. 11, 12 and 13 is placed between the semi-cylindrical jaws 30 and 32 and the cylinder 28 is compressed by closing the semi-cylindrical jaws on the cylinder as shown in FIGS. 9 and 10. Thereafter, a push rod 42 or the like is utilized to push the compressed cylinder 28 into the spaces 22 and 24 within the interiors of the adjacent vertebrae 12 and 14. When the compressed cylinder 28 enters the spaces 22 and 24, it restores to its normal cylindrical size as illustrated in FIGS. 11, 12 and 13.

Referring now to FIG. 11, once a solid compressible cylinder 28 of this invention is placed in the spaces 22 and 24 on one side of the vertebrae 12 and 14, a second solid compressible cylinder 28 is placed on the other side of the vertebrae 12 and 14 in accordance with the procedure described above.

The disc prosthesis of this invention, i.e., the two solid compressible cylinders 28, are identical in size, shape and composition. Each of the cylinders is formed of a solid rubbery compressible material which can include, but is not limited to, polyurethane, polyurethane coated with "SILASTIC™" (a rubbery coating), polypropylene, polyethylene, polytetrafluoroethylene or polydimethylsiloxane. Of these, polyurethane coated with "SILASTIC™" is preferred. "SILASTIC™" is a composition in physical character comparable to rubber prior to vulcanization, but containing organosilicon polymers and having excellent resistance to compression set. "SILASTIC™" is commercially available from Dow Corning Corp. of Midland, Mich. The coating of "SILASTIC™" makes the solid compressible cylinders inert with respect to the patient's body. Generally, the solid compressible cylinders deform at pressures in the range from about 5 psi to about 600 psi.

Once installed between adjacent vertebrae, the two solid compressible cylinders will not come out of the spaces within the interiors of the adjacent vertebrae. The cylinders have long lives, e.g., when the cylinders are formed of polyurethane coated with "SILASTIC™", they have a useful life of 20 years or more. However, if and when it is necessary to remove and replace the prosthesis due to infection or the like or the life span of the prosthesis has been reached, the procedure required is very simple and cost efficient. That is, the vertebrae containing the prosthesis are exposed and the prosthesis are broken up using a drill bit and removed by way of the partially circular space between the adjacent vertebrae. Thereafter, new solid compressible cylinders are inserted in the spaces within the interiors of the adjacent vertebrae as described above.

Referring now to FIGS. 14 through 18, an alternate apparatus to the pliers apparatus described above for compressing and pushing the disc prosthesis is illustrated. The alternate apparatus is a thumbscrew apparatus that compresses solid compressible cylinders 28 of the prosthesis into small cylindrical shapes and pushes them through the spaces 10 into the spaces 22 and 24 formed in the adjacent vertebrae 12 and 14.

Figure 14B:
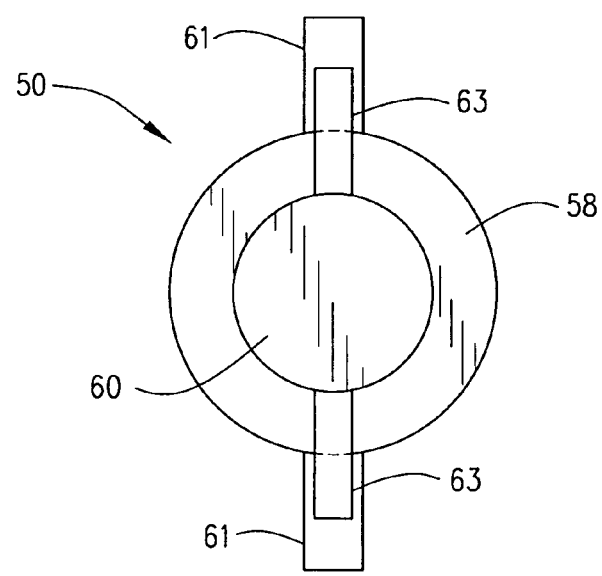
FIG. 14B is an end view of the thumbscrew apparatus illustrated in FIG. 14A.
Figure 15:
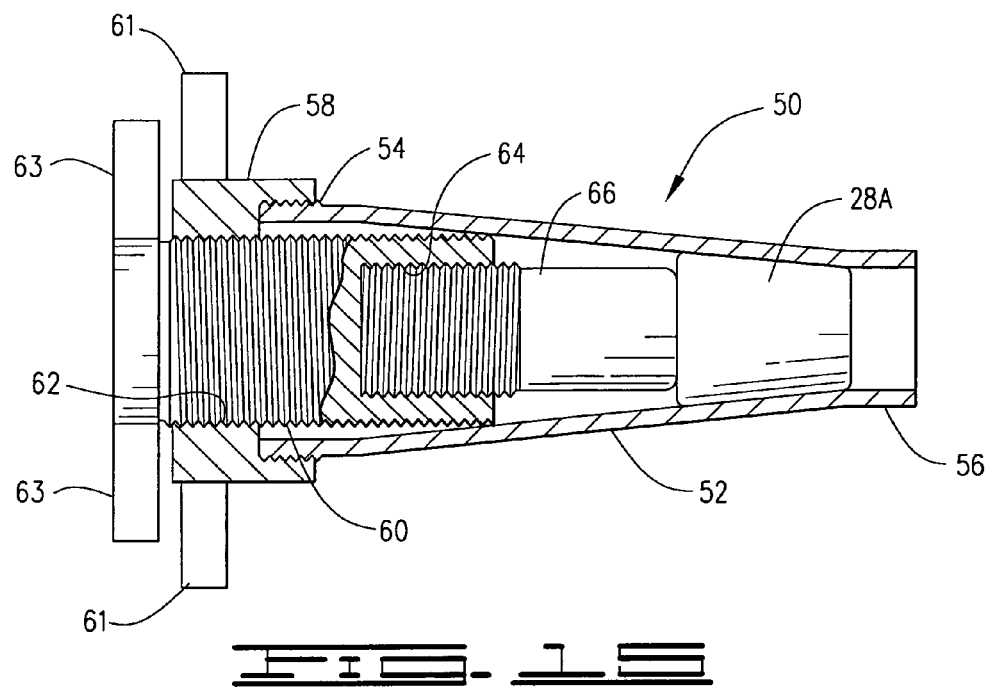
FIG. 15 is a side cutaway view of the thumbscrew apparatus illustrating a first step of its use whereby a first compressible cylinder is compressed and moved to the front of the apparatus.
Figure 16:
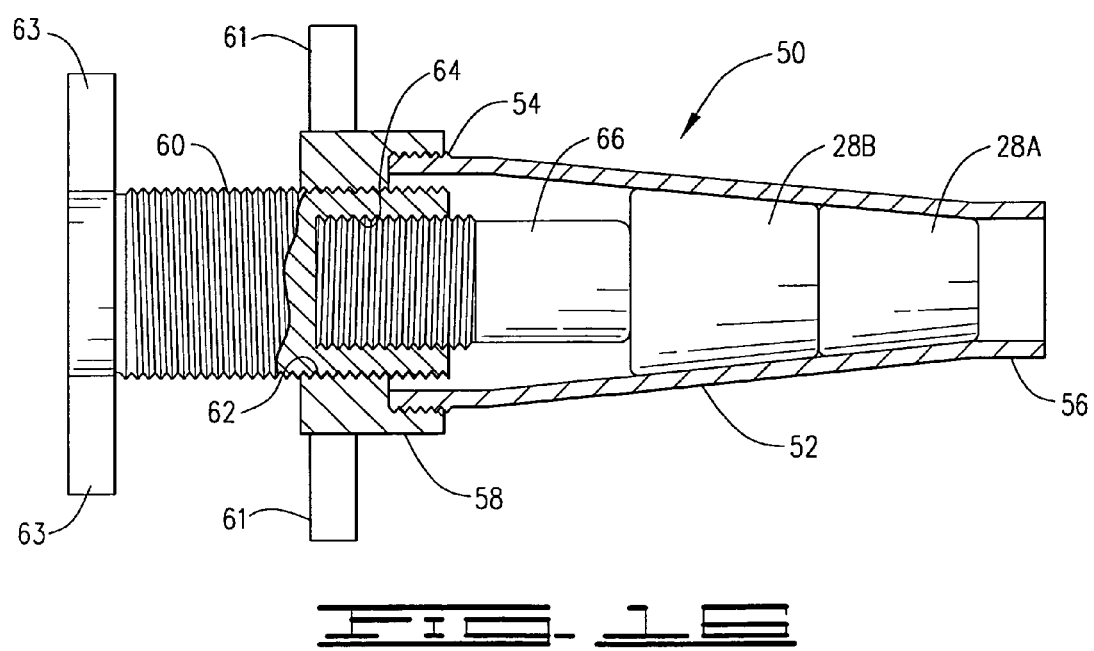
FIG. 16 is a side cutaway view of the thumbscrew apparatus illustrating a second step of its use whereby a second compressible cylinder is compressed and moved to a position adjacent to the first compressible cylinder.
Figure 17:
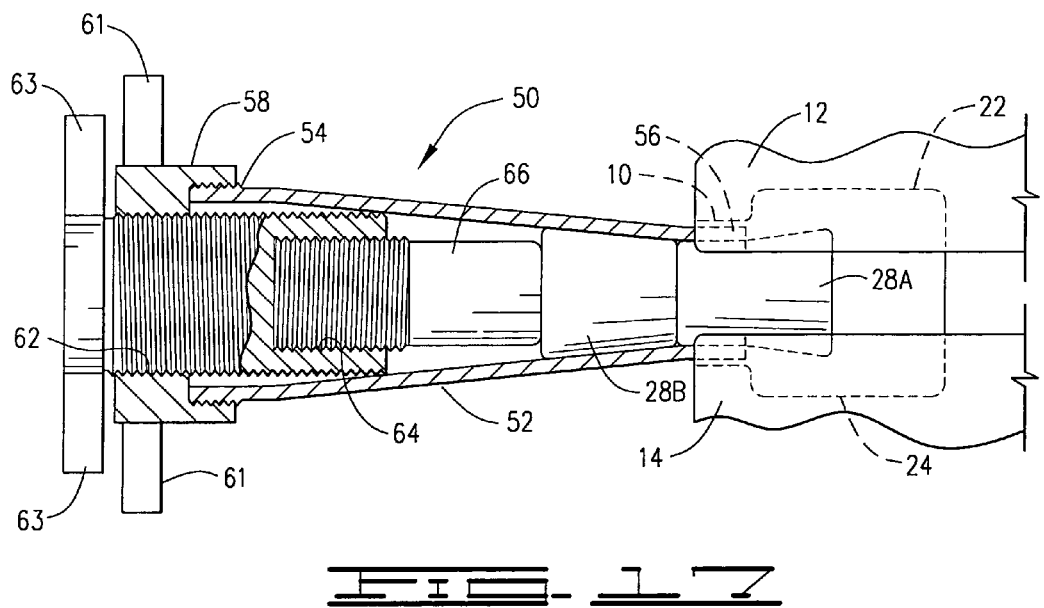
FIG. 17 is a side cutaway view of the thumbscrew apparatus after it has been inserted into the enlarged partially circular space between adjacent spinal vertebrae illustrating a third step of its use whereby the first and second compressible cylinders are moved forward and compressed further whereby the first compressible cylinder partially enters the spaces within the interiors of the adjacent vertebrae.
Figure 18:
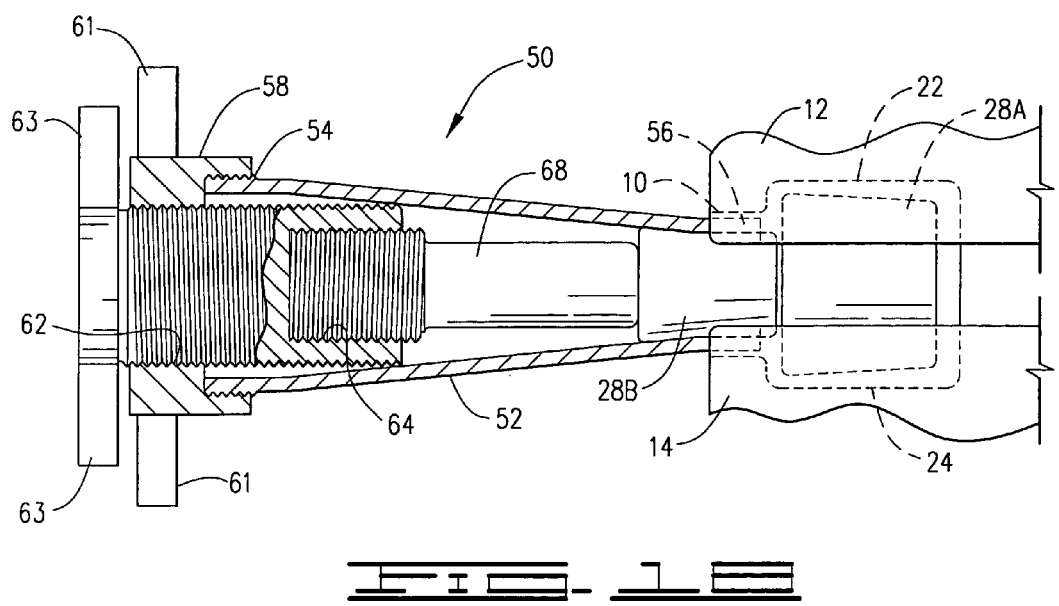
FIG. 18 is a side cutaway view of the thumbscrew apparatus illustrating a forth step of its use whereby the first compressible cylinder is moved into the additional spaces within the interiors of adjacent vertebrae and the second compressible cylinder is compressed further and moved forward in the thumbscrew apparatus.

Referring to FIGS. 14A and 14B, the thumbscrew apparatus 50 is illustrated. The thumbscrew apparatus 50 comprises an elongated tapered tube 52 having an externally threaded non-tapered large end 54 and a smooth non-tapered small end 56. The small end 56 is of a size that fits within the space 10 formed in the upper and lower vertebrae 12 and 14 as shown in FIGS. 17 and 18. An internally threaded cap 58 is threaded onto the externally threaded non-tapered large end 54 of the tapered tube 52, and an elongated threaded thumbscrew 60 is threaded into an internally threaded smaller opening 62 in the cap 58 as shown in FIGS. 15-18. The cap 58 and the thumbscrew 60 each include a pair of opposed handles 61 and 63, respectively, for turning the cap and thumbscrew Referring to FIGS. 15 through 18, the elongated threaded thumbscrew 60 includes an internally threaded counterbore 64 at its end within the tapered tube 52. Various sizes of push rods can be threaded into the thumbscrew 60 as required. In the procedure illustrated in FIGS. 15-18, a short, large diameter push rod 66 and a longer, smaller diameter push rod 68 are utilized. In that procedure, two solid compressible cylinders 28 are utilized in the thumbscrew apparatus 50 to place one of the cylinders in the spaces 22 and 24 formed in one side of the adjacent vertebrae 12 and 14 followed by the same procedure in the other side of the adjacent vertebrae as will be described herein below. However, as will be understood by those skilled in the art, one, two or more different push rods can be utilized to push a single solid compressible cylinder 28 in the thumbscrew apparatus into the spaces 22 and 24 formed in one side of the adjacent vertebrae 12 and 14 and the same process repeated in the other side of the adjacent vertebrae.

Still referring to FIGS. 15 through 18, the two solid compressible cylinder procedure for compressing a solid compressible cylinder 28 and placing it into the spaces 22 and 24 formed in adjacent vertebrae 12 and 14 is as follows. A first solid compressible cylinder 28 (referred hereinafter as compressible cylinder "28A") is placed in the thumbscrew apparatus 50 and is moved and compressed by the short, large diameter push rod 66 and the thumbscrew 60 to the forward position shown in FIG. 15. Thereafter, the push rod 66 and thumbscrew 60 are removed from the tube 52 and a second solid compressible cylinder 28 (referred to hereinafter as compressible cylinder "28B") is placed in the thumbscrew apparatus 50 and is moved and compressed by the short, large diameter push rod 66 and the thumbscrew 60 to the forward position adjacent to the compressible cylinder 28A as shown in FIG. 16. Thereafter, the small end of the tube 52 of the thumbscrew apparatus 50 is inserted into the space 10 formed in the upper and lower vertebrae 12 and 14 and the compressible cylinders 28A and 28B are moved forwardly to a position where the compressible cylinder 28A is pushed part way into the spaces 22 and 24 formed in adjacent vertebrae 12 and 14 as shown in FIG. 17. Thereafter, without removing the thumbscrew apparatus 60 from the space 10 in the upper and lower vertebrae 12 and 14, the push rod 66 and thumbscrew 60 are removed from the tube 52 and the longer, smaller diameter push rod 68 is substituted for the short, larger diameter push rod 66. The thumbscrew apparatus 50 is reassembled and the compressible cylinder 28A is pushed into the spaces 22 and 24 formed in the adjacent vertebrae 12 and 14 using the push rod 68. The thumbscrew apparatus 50 is removed from the space 10 and the above described procedure is repeated in the other side of the vertebrae 12 and 14.

The procedure that utilizes one solid compressible cylinder is the same as the two solid compressible cylinder procedure described above except that longer push rods or more than two push rods are utilized.

A great advantage of the present invention is that the procedure is carried out from the back of the patient and vascular or abdominal surgery is not required. The procedure allows the practitioner to see and avoid nerves and there are no prolonged side effects from the procedure.

A preferred method of this invention for placing a disc prosthesis comprising two solid compressible cylinders between adjacent spinal vertebrae comprises the steps of: (a) forming an enlarged partially circular space from the back and to one side of the space between adjacent vertebrae previously occupied by a degenerated disc; (b) forming additional spaces within the interiors of the adjacent vertebrae that intersect the enlarged space between the vertebrae; (c) placing a solid compressible cylinder in the spaces within the interiors of the adjacent vertebrae using thumbscrew apparatus for compressing the cylinder and then pushing the compressed cylinder into the spaces within the interiors of the adjacent vertebrae wherein the compressed cylinder expands to its original shape; and (d) repeating steps (a), (b) and (c) from the back and at the other side of the space between adjacent vertebrae.

Another method of the present invention for placing a disc prosthesis comprising two solid compressible cylinders between adjacent spinal vertebrae comprises the steps of: (a) forming an enlarged partially circular space from the back and to one side of the space between adjacent vertebrae previously occupied by a degenerated disc; (b) forming additional spaces within the interiors of the adjacent vertebrae that intersect the enlarged space between the vertebrae; (c) providing thumbscrew apparatus for compressing a solid compressible cylinder to a size slightly smaller than the enlarged substantially circular space between the adjacent spinal vertebrae; (d) compressing the solid compressible cylinder with the thumbscrew apparatus and pushing the compressed cylinder from the thumbscrew apparatus through the enlarged circular space between the adjacent spinal vertebrae into the spaces within the interiors of the adjacent vertebrae wherein the compressed cylinder expands to its original shape; and (e) repeating steps (a), (b), (c) and (d) from the back and from the other side of the space between adjacent vertebrae.

A spinal disc prosthesis of this invention comprises two solid compressible cylinders of a size for insertion in adjacent spaces within the interiors of adjacent vertebrae.

Thus, the present invention is well adapted to obtain the objects and advantages mentioned as well as those which are inherent therein. While numerous changes may be made by those skilled in the art, such changes are encompassed within the spirit of this invention as defined by the appended claims.

What is claimed is:

1. A method of placing a disc prosthesis comprising two solid compressible cylinders between adjacent spinal vertebrae comprising the steps of:
   (a) forming an enlarged partially circular space from the back and to one side of the space between adjacent vertebrae previously occupied by a degenerated disc;
   (b) forming additional spaces within the interiors of the adjacent vertebrae that intersect the enlarged space between the vertebrae;
   (c) placing a solid compressible cylinder in the spaces within the interiors of the adjacent vertebrae by compressing the solid compressible cylinder using a thumbscrew apparatus that compresses and pushes the compressed cylinder from the thumbscrew apparatus into the spaces within the interiors of the adjacent vertebrae wherein the compressed cylinder expands to its original shape; and
   (d) repeating steps (a), (b) and (c) from the back and at the other side of the space between adjacent vertebrae.

2. The method of claim 1 wherein the spaces within the interiors of the adjacent vertebrae are vertically aligned.

3. The method of claim 1 wherein the two solid compressible cylinders are formed of a solid compressible rubbery material.

4. The method of claim 1 wherein the two solid compressible cylinders are formed of a solid material comprising polyurethane, polypropylene, polyethylene, polytetrafluoroethylene or polydimethylsiloxane.

5. The method of claim 1 wherein the two solid compressible cylinders are formed of solid polyurethane coated with a material that makes the cylinders inert with respect to the patient's body.

6. The method of claim 1 wherein the enlarged substantially circular space between the adjacent spinal vertebrae is formed using a drill bit.

7. The method of claim 1 wherein the additional spaces within the interiors of the adjacent vertebrae are formed using a router having a very small shaft.

8. The method of claim 1 wherein the thumbscrew apparatus is used to compress the disc prosthesis to a size slightly smaller than the enlarged circular space between the adjacent spinal vertebrae and pushes the compressed disc prosthesis through the enlarged circular space between the adjacent spinal vertebrae into the spaces within the interiors of the adjacent vertebrae.

9. A method of placing a disc prosthesis comprising two solid compressible cylinders between adjacent spinal vertebrae comprising the steps of:
   (a) forming an enlarged partially circular space from the back and to one side of the space between adjacent vertebrae previously occupied by a degenerated disc;
   (b) forming additional spaces within the interiors of the adjacent vertebrae that intersect the enlarged space between the vertebrae;
   (c) providing a thumbscrew apparatus for compressing a solid compressible cylinder to a size slightly smaller than the enlarged substantially circular space between the adjacent spinal vertebrae;
   (d) compressing the solid compressible cylinder with the thumbscrew apparatus and pushing the compressed cylinder from the apparatus through the enlarged circular space between the adjacent spinal vertebrae into the spaces within the interiors of the adjacent vertebrae wherein the compressed cylinder expands to its original shape; and
   (e) repeating steps (a), (b), (c) and (d) from the back and from the other side of the space between adjacent vertebrae.

10. The method of claim 9 wherein the spaces within the interiors of the adjacent vertebrae are vertically aligned.

11. The method of claim 9 wherein two solid compressible cylinders are formed of a solid compressible rubbery material.

12. The method of claim 9 wherein the two solid compressible cylinders are formed of a solid material comprising polyurethane, polypropylene, polyethylene, polytetrafluoroethylene or polydimethylsiloxane.

13. The method of claim 9 wherein the compressible cylinders are formed of solid polyurethane coated with a material that makes the cylinders inert with respect to the patient's body.

14. The method of claim 9 wherein the enlarged substantially circular space between the adjacent spinal vertebrae is formed using a drill bit.

15. The method of claim 9 wherein the additional spaces within the interiors of the adjacent vertebrae are formed using a router having a very small shaft.

16. The method of claim 9 wherein the thumbscrew apparatus compresses the disc prosthesis to a size slightly smaller than the enlarged circular space between the adjacent spinal vertebrae and the compressed disc prosthesis is pushed out of the thumbscrew apparatus through the enlarged circular space between the adjacent spinal vertebrae into the spaces within the interiors of the adjacent vertebrae wherein the disc prosthesis expands therein.

\* \* \* \* \*